(12) United States Patent
Carmichael et al.

(10) Patent No.: US 8,947,098 B2
(45) Date of Patent: Feb. 3, 2015

(54) IONIZATION GAUGE WITH EMISSION CURRENT AND BIAS POTENTIAL CONTROL

(75) Inventors: Larry K. Carmichael, Platterville, CO (US); Jesse A. Weber, Arvada, CO (US); John H. Henry, Broomfield, CO (US); Michael N. Schott, Loveland, CO (US); Gerardo A. Brucker, Longmont, CO (US); Kenneth D. Van Antwerp, Jr., Colorado Springs, CO (US)

(73) Assignee: MKS Instruments, Inc., Andover, MA (US)

( * ) Notice: Subject to any disclaimer, the term of this patent is extended or adjusted under 35 U.S.C. 154(b) by 0 days.

(21) Appl. No.: 13/051,430

(22) Filed: Mar. 18, 2011

(65) Prior Publication Data

US 2011/0163754 A1 Jul. 7, 2011

Related U.S. Application Data

(63) Continuation of application No. PCT/US2009/056612, filed on Sep. 11, 2009.

(60) Provisional application No. 61/192,684, filed on Sep. 19, 2008.

(51) Int. Cl.
*G01L 21/30* (2006.01)
*G01L 21/32* (2006.01)
*H01J 41/02* (2006.01)

(52) U.S. Cl.
CPC ............... *G01L 21/32* (2013.01); *H01J 41/02* (2013.01); *G01L 21/30* (2013.01)
USPC ........................................................ 324/460

(58) Field of Classification Search
CPC ................................ G01L 21/30; H01J 41/02

USPC .......................................................... 324/460
See application file for complete search history.

(56) References Cited

U.S. PATENT DOCUMENTS 4,093,913 A 6/1978 O'Neal, III
4,636,680 A 1/1987 Bills et al.
(Continued)

FOREIGN PATENT DOCUMENTS

EP 1 698 878 A1 9/2006
JP S63151834 6/1988
(Continued)

OTHER PUBLICATIONS

Transmittal of International Preliminary Report on Patentability and Written Opinion, International Application No. PCT/US2009/056612 mailed on Mar. 31, 2011.
(Continued)

*Primary Examiner* — Jeff Natalini
(74) *Attorney, Agent, or Firm* — Hamilton, Brook, Smith & Reynolds, P.C.

(57) ABSTRACT

An ionization gauge that measures pressure has an electron source that emits electrons, and an anode that defines an ionization space. The gauge also includes a collector electrode to collect ions formed by an impact between the electrons and a gas and to measure pressure based on the collected ions. The electron source is dynamically varied in emission current between a plurality of emission levels dependent on pressure and a second parameter other than pressure. The ionization gauge may also vary various operating parameters of the gauge components according to parameters stored in a non-volatile memory and selected by a user.

18 Claims, 5 Drawing Sheets

(56) References Cited

U.S. PATENT DOCUMENTS

| | | | |
|---|---|---|---|
| 4,652,752 A | 3/1987 | Ino et al. | |
| 4,910,402 A | 3/1990 | McMillan | |
| 5,250,906 A | 10/1993 | Bills et al. | |
| 5,331,682 A * | 7/1994 | Hsieh | 378/19 |
| 5,475,227 A | 12/1995 | LaRue | |
| 5,608,384 A * | 3/1997 | Tikijian | 340/632 |
| 5,801,535 A | 9/1998 | Bills | |
| 6,081,121 A * | 6/2000 | Bills | 324/460 |
| 6,433,553 B1 * | 8/2002 | Goeckner et al. | 324/464 |
| 6,515,482 B2 * | 2/2003 | Kawasaki | 324/460 |
| 7,030,619 B2 | 4/2006 | Arnold et al. | |
| 7,352,187 B2 * | 4/2008 | Knapp et al. | 324/460 |
| 2001/0011890 A1 * | 8/2001 | Kawasaki | 324/460 |
| 2002/0153820 A1 | 10/2002 | Ellefson et al. | |
| 2005/0030044 A1 | 2/2005 | Correale | |
| 2005/0277789 A1 * | 12/2005 | Bloomfield et al. | 564/4 |
| 2006/0101836 A1 | 5/2006 | Tanaka | |
| 2006/0122797 A1 * | 6/2006 | Waymouth et al. | 702/65 |
| 2008/0011606 A1 | 1/2008 | Zhang et al. | |
| 2008/0018337 A1 * | 1/2008 | Carmichael et al. | 324/460 |
| 2008/0079436 A1 * | 4/2008 | Gollhardt et al. | 324/457 |

FOREIGN PATENT DOCUMENTS

| | | |
|---|---|---|
| JP | 2006021025 | 1/1994 |
| JP | H06129934 | 5/1994 |
| JP | H10213509 | 8/1998 |
| JP | 2011083661 | 3/1999 |
| JP | H11183296 | 7/1999 |
| JP | H11339699 | 12/1999 |
| JP | 2001-015060 | 1/2001 |
| JP | 2003050176 | 2/2003 |
| JP | 2003106901 | 4/2003 |
| JP | 2007073395 | 3/2007 |
| JP | 2008170175 | 7/2008 |
| WO | WO 2008/010887 A2 | 1/2008 |

OTHER PUBLICATIONS

"Notification of Transmittal of the International Search Report and the Written Opinion of the International Searching Authority, or the Declaration," mailed Feb. 10, 2010 for International Application No. PCT/US2009/056612.

"Introduction to Bayard-Alpert Ionization Gauges," *Granville-Phillips Helix Technology Corporation*, consisting of 4 pages (1999).

"303 Vacuum Process Controller," Instructional Manual P/N 303035-101, *Granville-Phillips*, consisting of 11 pages (1983, revised 1995).

Supplementary European Search Report, EP 09 81 5009, dated Jul. 5, 2012, 6 pages.

* cited by examiner

IONIZATION GAUGE WITH EMISSION CURRENT AND BIAS POTENTIAL CONTROL

RELATED APPLICATIONS

This application is a continuation of International Application No. PCT/US2009/056612, which designated the United States and was filed on Sep. 11, 2009, published in English, which claims the benefit of U.S. Provisional Application No. 61/192,684, filed on Sep. 19, 2008.

The entire teachings of the above application(s) are incorporated herein by reference.

BACKGROUND OF THE INVENTION

Ionization gauges, more specifically Bayard-Alpert (BA) ionization gauges, are the most common non-magnetic means of measuring very low pressures. The gauges have been widely used worldwide. These gauges were disclosed in 1952 in U.S. Pat. No. 2,605,431, which is herein incorporated by reference in its entirety. A typical ionization gauge includes a cathode filament as an electron source, an anode, and an ion collector electrode. For the BA ionization gauge, the electron source is located outside of an ionization space or an anode volume which is defined by a cylindrical anode screen. The ion collector electrode is disposed within the anode volume. Electrons travel from the electron source to and through the anode, cycle back and forth within the anode, and are consequently retained within the anode.

In their travel, the electrons collide with molecules and atoms of gas that constitute the atmosphere whose pressure is to be measured. This contact between the electrons and the gas creates ions. The ions are attracted to the ion collector electrode, which is typically connected to ground. The pressure of the gas within the atmosphere can be calculated from ion and electron currents by the formula $P=(1/S) (I_{ion}/I_{electron})$, where S is a coefficient with the units of 1/Torr and is characteristic of a particular gauge geometry, electrical parameters, and pressure range.

Generally, in existing dual filament hot-cathode ionization gauges, each filament is operated at two different emission currents with the first being about 4 mA and the second current level being about 100 µA. Generally, the ionization gauge is operated to switch between these two current levels based on adjustable preset pressure levels that are manually set by the user. In another system, the emission current varied step-wise through ten levels between minimum and maximum levels specified by a user. The purpose of these multiple current levels is to have the most sensitivity for the ionization gauge in the respective pressure range of operation.

SUMMARY OF THE INVENTION

The operational lifetime of a typical ionization gauge is approximately ten years when the gauge is operated in benign environments. However, these same gauges fail in minutes or hours when operated at too high a pressure or during operation in gas types that degrade the emission characteristics of the electron source cathode. Cathode interactions with the gauge environment can lead to decreased operational life. The oxide coating on the cathode can degrade when exposed to water vapor. Degradation of the oxide coating dramatically reduces the number of electrons generated by the cathode. Exposure to water vapor may even result in the complete burnout of a tungsten cathode.

Sputtering is also a problem when operating the ionization gauge at high pressures, such as above $10^{-4}$ Torr in argon. Sputtering is a problem at high pressure since there is more gas to ionize. This sputtering is caused by high impact energies between ions and components of the ionization gauge. Ions with a high energy may impact a tungsten material that forms a collector post of the ionization gauge. This results in atoms being ejected from the collector post and envelope surfaces. This ejection can coat the cathode filament or components of the gauge, which is greatly disfavored.

It has been observed that the rate of sputtering per unit time is a function of the particular emission current that is provided to the cathode filament for a specific pressure. Low sputtering rates are desired, but they are desired while having a sufficient filament emission current to measure pressure correctly. This sufficient current is in order to get a sufficient signal for the operation of the ionization gauge and, moreover, to provide for a sensitive ionization gauge over multiple different pressure measurement ranges.

As the cathode filament ages or becomes contaminated, it must be heated to higher temperatures in order to generate a desired level of emission current. That additional heating can further stress the cathode filament and lead to its failure.

There is provided an ionization gauge to measure pressure, the gauge having an electron source (for example, a cathode filament), an anode, and a collector electrode. The electron source may be dynamically varied in emission current to reduce stress on the cathode filament and to prevent damaging the gauge or components from sputtering while operating at a predetermined pressure level.

An ionization gauge to measure pressure may comprise an electron source that emits electrons, an anode that defines an ionization space and a collector electrode to collect ions formed by an impact between the electrons and gas in the ionization space. A controller may actively control emission current from the source during operation in response to a sensed parameter other than pressure that is sensed during operation. Alternatively or in addition, the controller may define operation profiles including bias voltages that are selectable by an end user. The controller may control emission current from the electron source during operation in response to a control signal that anticipates a change in pressure due to a process step.

The controller may control emission current as a function of pressure. The control may be in a continuously variable manner or as a step function. The function of pressure may be selectable by a user.

The parameter other than pressure may be a species of gas in the environment being measured.

A parameter other than pressure may be cathode temperature of the electron source. The emission current may be controlled to gradually increase during startup. Cathode temperature may be indicated by electrical resistance of the cathode by an infrared sensor, or by an optical parameter of the cathode.

The parameter other than pressure may be collector current through the collector electrode. The emission current may be controlled to maintain the collector current fixed, with the emission current indicating pressure. In a first pressure range, the collector current may be held to a fixed level and, in a second pressure range, the collector current may be allowed to vary. In the second pressure range, the emission current may be fixed or variable.

Plural emission current profiles may be stored in memory and selected by a user.

The ionization gauge may be used in a process in which a tool is evacuated to perform processes on a substrate in the tool. The ionization gauge may be used in a process where a parameter of the process is measured using an analytical tool.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
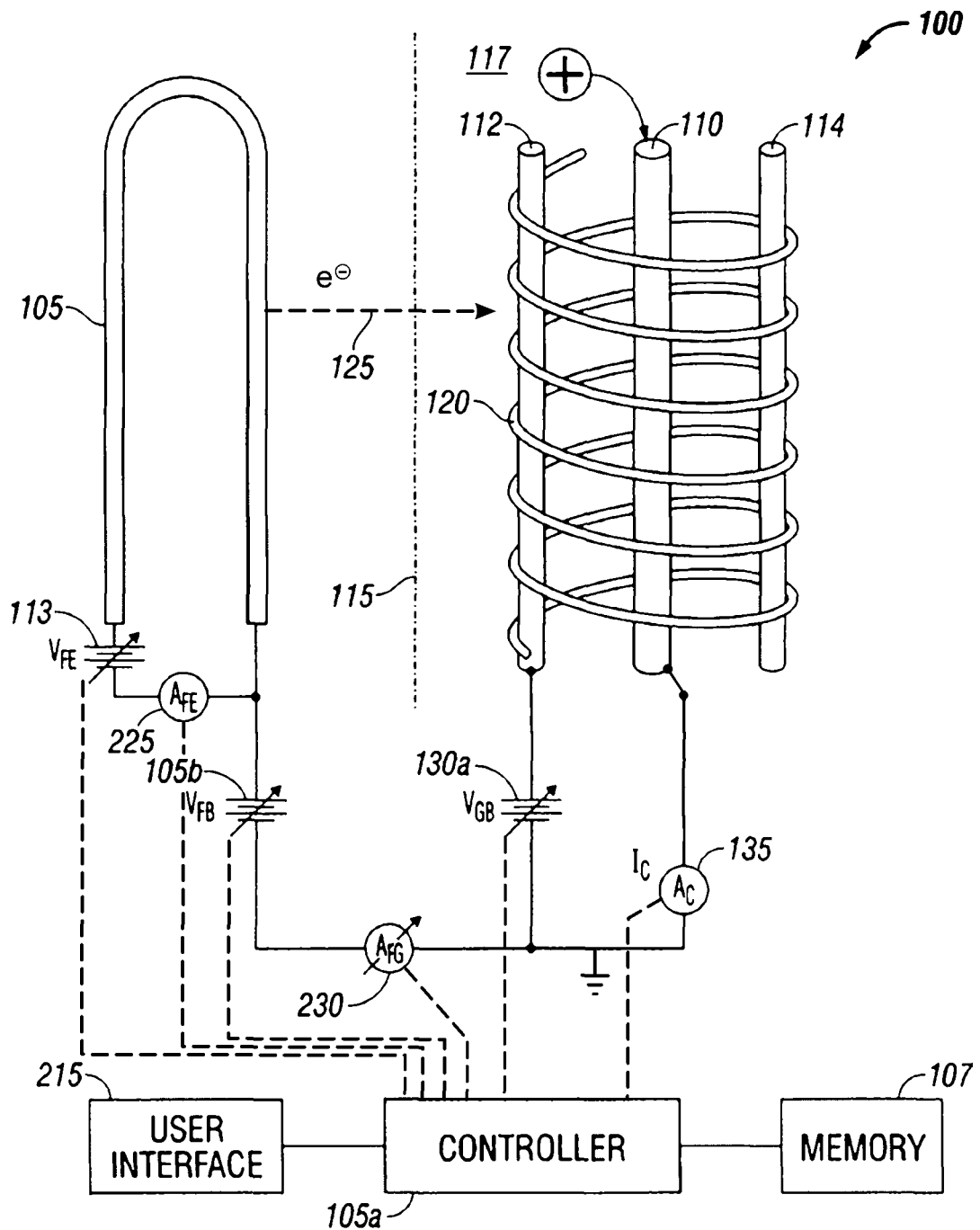
FIG. 1 shows an ionization gauge embodying the invention that dynamically adjusts an emission current.

A description of preferred embodiments of the invention follows. Generally, as shown in FIG. 1, an ionization gauge 100 of the present disclosure has at least one electron source 105 and at least one collector electrode 110. The electron source 105 may be separated from the at least one collector electrode 110 by an optional isolation material 115 which prevents molecules and atoms of gas within a measurement chamber 117 from degrading the electron source(s) 105. The ionization gauge 100 also includes an ionization volume, specifically within an anode 120 supported by posts 112 and 114. Anode 120 and the collector electrode 110 components may have various different configurations, and the gauge 100 is not limited to FIG. 1. In one embodiment, the ionization gauge 100 is a Bayard-Alpert type gauge, or an ionization gauge 100 where a heated cathode filament 105 is used to emit electrons toward an anode grid 120. However, it should be appreciated that the gauge 100 is not limited to any specific ionization gauge configuration and the present disclosure encompasses several different types of ionization gauges.

The Bayard-Alpert type gauge 100 is based on the ionization of gas molecules by a constant flow of electrons 125. The negatively charged electrons shown as reference numeral 125 are emitted at a well-controlled selectable rate from a heated cathode 105, and may be released, or accelerated toward a positively charged anode 120. The electrons 125 pass into and through the anode 120 and then cycle back and forth within the anode 120. The electrons 125 are retained within the ionization volume of the anode 120. In this space, the electrons 125 collide with the gas molecules to produce positively charged ions. These ions are collected by the one or more ion collector(s) 110. Collector 110 is nearly at ground potential, which is negative with regard to the positively charged anode 120. However, this arrangement is not limiting and collector 110 may have various potential differences with respect to the anode 120. At a constant cathode to anode voltage and electron emission current, the rate that positive ions are formed is directly correlated to the density of the gas in the gauge 100. This signal from the collector electrode 110 is detected by an ammeter 135, which is calibrated in units of pressure, for all pressure readings.

The geometrical shape of the cathode 105 can be a linear ribbon, a linear wire, a straight ribbon, a curved ribbon, a hairpin wire, or any other acceptable cathode shape known in the art. In one embodiment, the cathode 105 is resistively heated to incandescence with an electrical current from cathode heating power supply 113. The thermionically emitted electrons 125 may be released, or accelerated or directed into the measurement chamber 117 towards anode 120. Electrons 125 have a sufficient energy which allows the electrons to be transmitted to the ionization volume of anode 130 and have sufficient energy to enter the anode 120.

A controller 105a is connected to the cathode bias supply 105b to maintain a cathode bias voltage of about 30 volts. A heating voltage from power supply 113 is also controlled by controller 105a during normal operation. Once the cathode 105 is sufficiently heated, the controller 105a controls the heating of cathode 105 to maintain the appropriate electron current. The cathode bias voltage 105b and anode voltage bias 130a provide a sufficient voltage difference from the cathode 105 to the anode 130 to accelerate electrons 125 toward the anode grid 120. Ionization occurs over an energy spread both higher and lower than the nominal design energy; see Section 5.7 on ionization gauges in *Scientific Foundations of Vacuum Technique* by Saul Dushman, 1962, which is herein incorporated by reference in its entirety.

A user interface 215 may include one or more buttons, one or more knobs, or a touch screen interface. It may be a personal computer. The present ionization gauge 100 can be used in cluster tools and sputtering deposition environments for semi-conductor processing operations and for manufacturing flat panel displays. In these environments, the gas species and specific operating parameters including pressure, temperature, gas species and other application specific parameters of the manufacturing processes are kept strictly confidential. The applications, and the method of implementing the applications are trade secrets on behalf of an individual manufacturer. The manufacturer is reluctant to share these confidential parameters with third parties as they may provide a competitive advantage. Accordingly, through the user interface, the present ionization gauge 100 permits the manufacturer to vary several user defined operating parameters of the ionization gauge 100 without specifically disclosing manufacturing trade secrets to third parties.

In one embodiment, the user may select parameters for the ionization gauge, such as emission current and ionization potential. The user may select a single emission current value or a range of emission current values, a single ionization potential value or a range of ionization potential values. This selection can occur using the user interface input device 215.

In another embodiment, a type of application can be specified for the ionization gauge 100 using the specific input device on the user interface 215. The type of application may refer to the gas type that is in the cluster tool environment, a gas mixture or the specific process being performed at the moment in the cluster tool, such as, for example, a sputtering deposition application. Here, the gauge 100 has a cathode excitation voltage supply 113, a cathode excitation current ammeter 225, a cathode/anode ammeter 230, an anode bias voltage supply 130a, and an ammeter 135. Here, for a specific high pressure sputtering application (with specific operating parameters) one or more of the cathode excitation voltage supply 113, the cathode excitation current 225, the cathode/anode current 230, or the anode bias voltage supply 130a can be individually manipulated by the controller 105a based on settings stored in the memory 107. In response to this input, the controller 105a accesses a lookup table in the memory 107 for preprogrammed set points for the various ionization gauge components that are optimal for the specific gas type or the specific cluster tool application. These may include, but are not limited to, the optimal or maximum cathode temperature, the maximum emission current or other parameters that have been preprogrammed into the memory 107. Thereafter, the controller 105a will control one or more of the previously mentioned ionization gauge components according the optimal parameters in memory 107, or those parameters programmed by the user.

Other parameters which can be varied may include a temperature of the cathode, a maximum pressure range, collector electrode current, a signal to noise ratio, peak gas ionization level, a minimum emission current, gas type, specific processes, or specific applications.

The controller 105a of the ionization gauge 100 may also further include a feedback function. The controller may monitor one or more parameters of the ionization gauge components, and when a desired parameter exceeds or meets a trigger value stored in the memory 107, then the controller 105a may change one or more settings of the ionization gauge 100. For example, the controller 105a may monitor the temperature of the cathode 105. The controller 105a may compare the temperature of the cathode 105 to a set temperature trigger value in the memory 107. If the temperature of the cathode 105 exceeds this set trigger value, the controller 105a may control emission current to reduce the temperature of the cathode 105 and change other parameters to reduce sputtering while maintaining an acceptable signal to noise ratio. Additionally, this trigger value for the maximum cathode temperature may be different for argon gas than other gases, and may change depending on the specific gas species mixture of gases, or the pressure detected in the cluster tool or chamber. These additional parameters may be stored in a profile in the non-volatile memory 107. Preferably, multiple different profiles are stored in the memory 107, and which can be accessed by the controller 105a or selected using the user interface 215.

Figure 2:
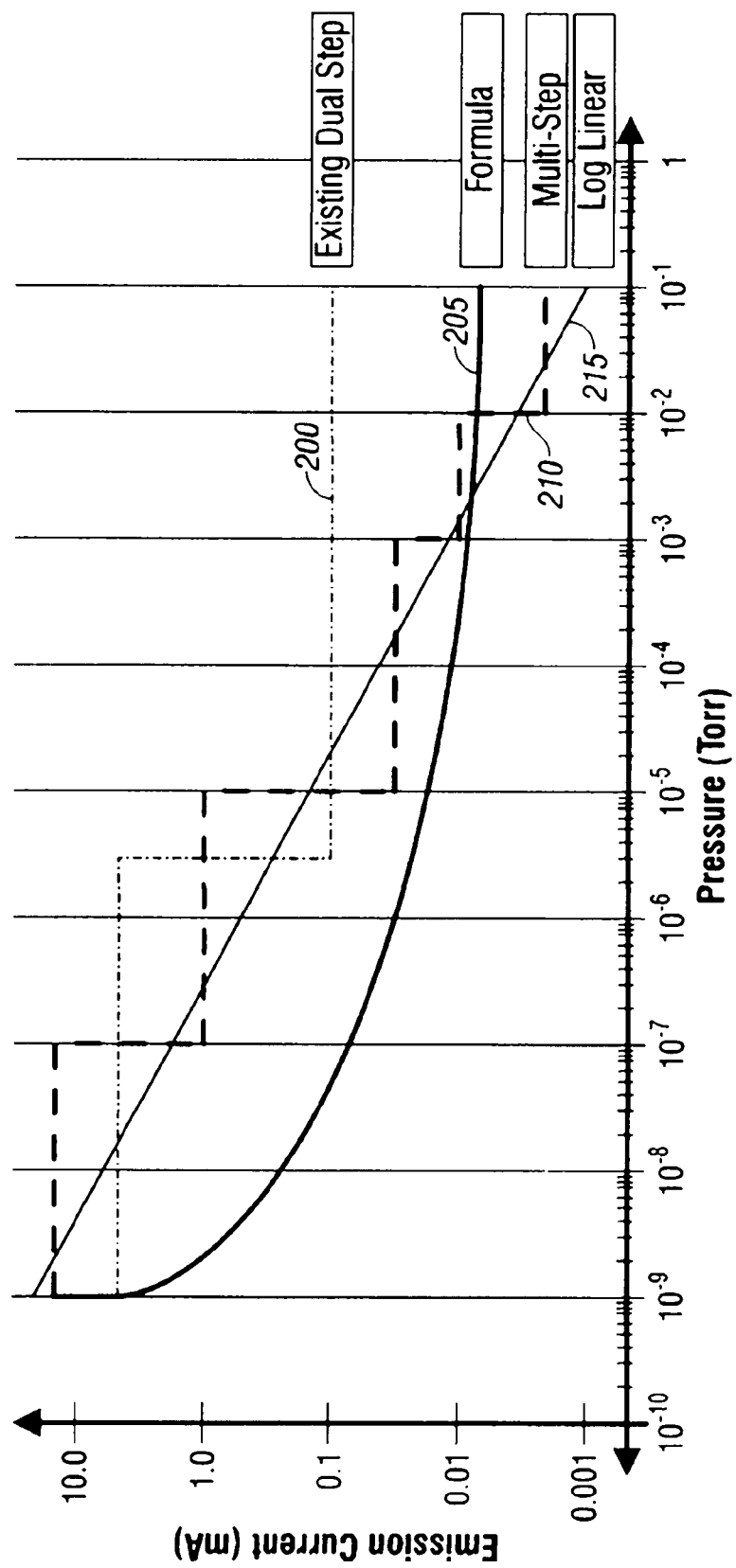
FIG. 2 shows several plots of the emission current against pressure.

Preferably, the controller 105a (coupled to the heating voltage source 113) dynamically adjusts an emission current supplied from the cathode 105 based on detected pressure levels to reduce sputtering and improve a life of the ionization gauge. One or more profiles such as illustrated in FIG. 2 may be stored in memory 107 for selection by a user. The detected pressure may be from the ammeter 135 (the ionization gauge 100 itself) or may be from a reading from a separate gauge. Based on the pressure, the controller 105a will adjust the emission current as shown in FIG. 2.

Turning now to FIG. 2, there is shown a graph of an emission current supplied to the cathode 105 over several decades of operating pressure as reference numerals 200, 205, 210, and 215. Turning to the first emission current plot 200, there is shown a previously discussed existing dual step emission from cathode 105 according to the prior art. Here from $10^{-9}$ Torr to about $10^{-6}$ Torr, about 4.0 mA is supplied as emission current, while at about $10^{-5}$ to $10^{-1}$ Torr, about 0.1 mA is supplied as emission current from the cathode 105. This prior art emission current may cause an unacceptable level of sputtering depending on a pressure of the gas in the ionization gauge 100.

The present ionization gauge 100 varies emission current from cathode 105 as a function of pressure to extend life of the ionization gauge 100. This dynamic varying of the emission current based on pressure, reduces and minimizes the effect of self sputtering due to operation of the ionization gauge 100 at high pressures. Here, in the second plot 205, there is shown a continuously variable "formula based" emission current plot. Here from $10^{-9}$ Torr, about 10.0 mA are supplied as an emission current, while at about $10^{-8}$ Torr about greater than 0.1 mA is supplied as emission current, and while at about $10^{-5}$ to $10^{-1}$ Torr about 0.01 mA is supplied as emission current from the cathode 105. This is advantageous as this allows for an acceptable emission current to detect pressure to obtain a relatively strong signal while at the same time preventing an unacceptable level of sputtering while operating at high pressures.

Here, in the third plot 210, there is shown a multi-step emission current plot. Here from $10^{-9}$ Torr to about $10^{-7}$, about 10.0 mA is supplied as an emission current while at about $10^{-7}$ Torr to about $10^{-5}$ Torr about 1.0 mA is supplied as emission current. In the third step, at about $10^{-5}$ Torr to $10^{-3}$ Torr about 0.03 mA is supplied and at about $10^{-3}$ Torr to $10^{-2}$ Torr, about 0.01 mA is supplied as emission current from the cathode 105 of FIG. 1. Then, from $10^{-2}$ Torr to about $10^{-1}$ Torr about 0.003 mA is applied as emission current. In comparison to the dual step method plot of the prior art shown as reference number 200, with the multistep plot 210, only a fraction of the emission current is supplied from the cathode 105 at relatively higher pressures. This is very advantageous. The ionization gauge 100 provides for a proper emission current. This current level develops a strong signal. The signal is sufficiently strong to detect pressure, while preventing an unacceptable level of sputtering while operating at high pressures.

Here, in the fourth plot 215, there is shown a linear continuously variable dynamic emission current plot. Here from $10^{-9}$ Torr to about $10^{-7}$ Torr, the emission current varies from about 10.0 mA to about 1.0 mA. At about $10^{-7}$ Torr to about $10^{-5}$ Torr about 1.0 Amp to about 0.1 mA is supplied as emission current from the cathode 105. At about $10^{-5}$ Torr to $10^{-3}$ Torr a range from about 0.1 to 0.01 mA is supplied. At about $10^{-3}$ Torr to $10^{-1}$ Torr, a range from about 0.01 mA to 0.001 mA is supplied as emission current from the cathode 105.

Generally, cathode filaments are formed of either coated iridium or uncoated tungsten. The former operate in the temperature range of 600°-1000° C. and glow red or orange; whereas, the tungsten cathodes operate in the temperature range of 1500°-2000° C. and glow yellow. As the cathodes age or become contaminated, they become less emissive of electrons. To maintain a desired emission current, the excitation voltage 113 applied to the cathode may be increased to increase the temperature of the cathode and thus the emission. However, if heated too much, the cathode may fail.

In accordance with certain embodiments, the temperature of the cathode filament is sensed and, if the temperature becomes too high, the excitation voltage and thus the emission current are reduced. The reduction results in an emission current that is less than the optimum as determined by a selected emission current profile, but the lost sensitivity is accepted as a cost of avoiding destruction of the cathode filament.

Figure 3:
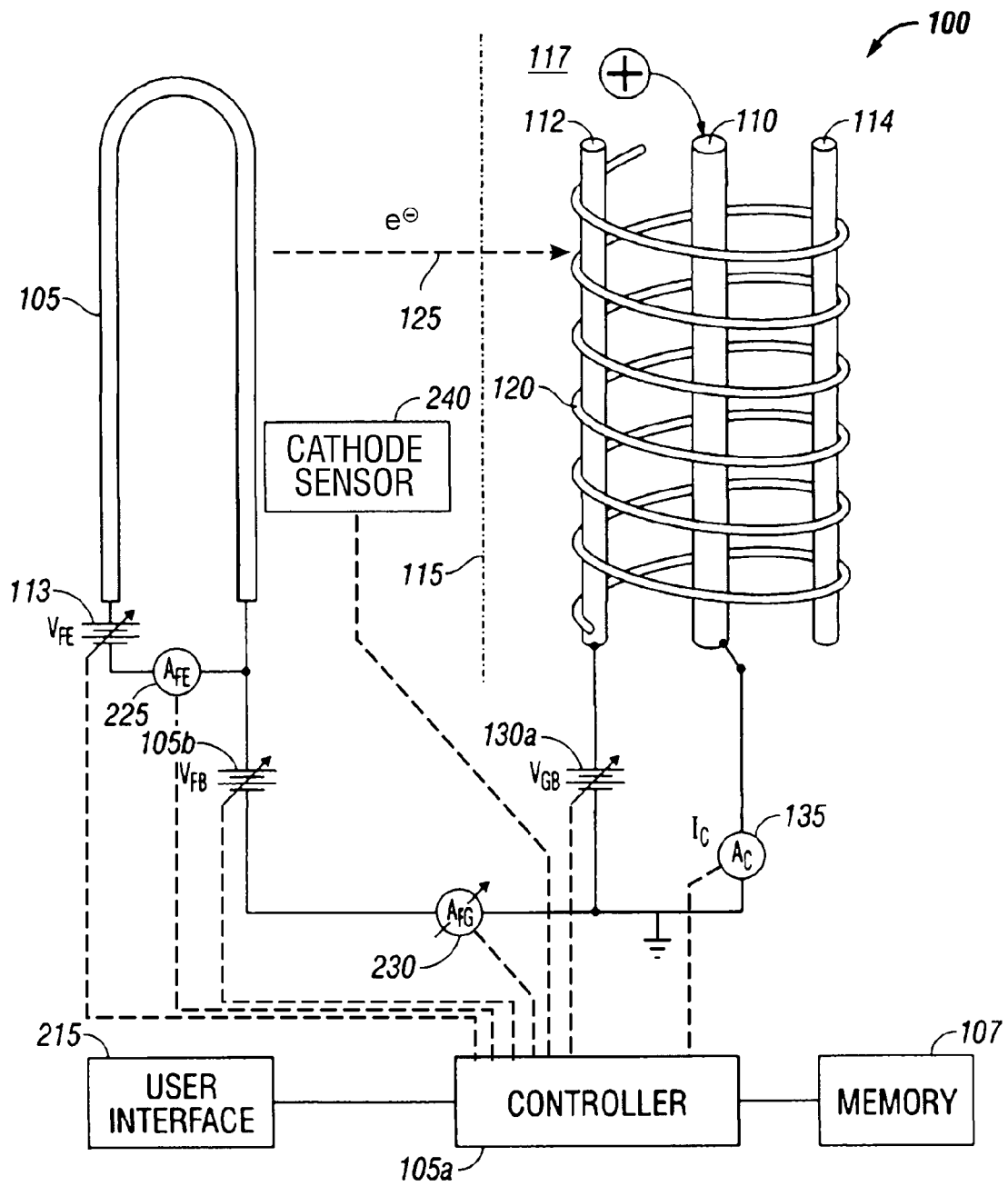
FIG. 3 shows an ionization gauge embodying the invention with a sensor for detecting a parameter of the filament.

The cathode filament temperature is directly related to its electrical resistance. Therefore, it can be sensed by the ratio of excitation voltage 113 to cathode current 225. An alternative temperature sensor is illustrated in FIG. 3. The sensor 240 may, for example, be an infrared flux sensor that provides a temperature reading. Alternatively, the sensor 240 may be a color sensor. As a coated iridium cathode becomes too hot, it becomes yellow; as a tungsten cathode becomes too hot, it becomes white. As those colors are sensed, the system can reduce the excitation voltage 113 and thus the temperature of the cathode at a loss of emission current.

During operation, cathode 105 often will be switched on or increased from a present emission level to a target emission level. Generally, this is not an issue if the present emission level and the target emission level are relatively close in values. However, if the present emission level and the target emission level are separated by a predetermined amount, the cathode 105 can undergo a rapid temperature change per unit time, and this can stress the cathode 105 (attributed to the temperature change) and damage the cathode 105.

Preferably, in this embodiment, the temperature change of the cathode 105 is detected by a controller 105*a*, and if a certain temperature difference or stress on the cathode 105 is detected, then the controller 105*a* will correctly control the emission current delivered from the cathode 105 to prevent damaging the cathode 105. In a first embodiment, the controller 105*a* may dynamically increase the emission current from a current level to the target level in a series of steps as previously discussed or in a linear or non-linear manner, or by a preset formula of ionization gauge variables.

In another embodiment, the voltage or current change of the cathode 105 is detected by a controller 105*a*, and if a certain predetermined difference in current is detected between a current level and a target level then the controller will dynamically control the emission current delivered from the cathode 105 using the excitation voltage 113. The controller 105*a* may increase the emission current from a current level to the target level in a series of steps as previously discussed or in a linear or non-linear manner.

In other embodiments, the cathode 105 will not exceed a specific percentage change, or predetermined rate of change of at least one of the cathode temperature or voltage or current delivered to the cathode 105 or emission current (detected as the cathode to anode current detected by ammeter 230). A specific voltage value or a predetermined amount of current supplied to or from the cathode 105 is detected by a controller 105*a*. If a target set point of the rate of change or the specific percentage is exceeded, then the controller 105*a* will dynamically control the heating supply 113 to control the heating current delivered to the cathode 105, and this will reduce the amount of emission current so as to not exceed the target set point. The controller 105*a* may cap the emission current at a predetermined level, and prevent incrementing the emission current further. The emission current is prevented from exceeding the desired set point to prevent damaging the cathode filament 105 by stressing the cathode, or, alternatively, to prevent sputtering.

It should be appreciated that the present teachings also may encompass operation during a degas mode of the ionization gauge 100 where, in a high vacuum, the anode voltage and emission current are increased to create a large number of electrons to clean the inner walls and surfaces of the gauge. Here, the degas emission current supplied from the cathode 105 may also be dynamically controlled as previously described.

Figure 4:
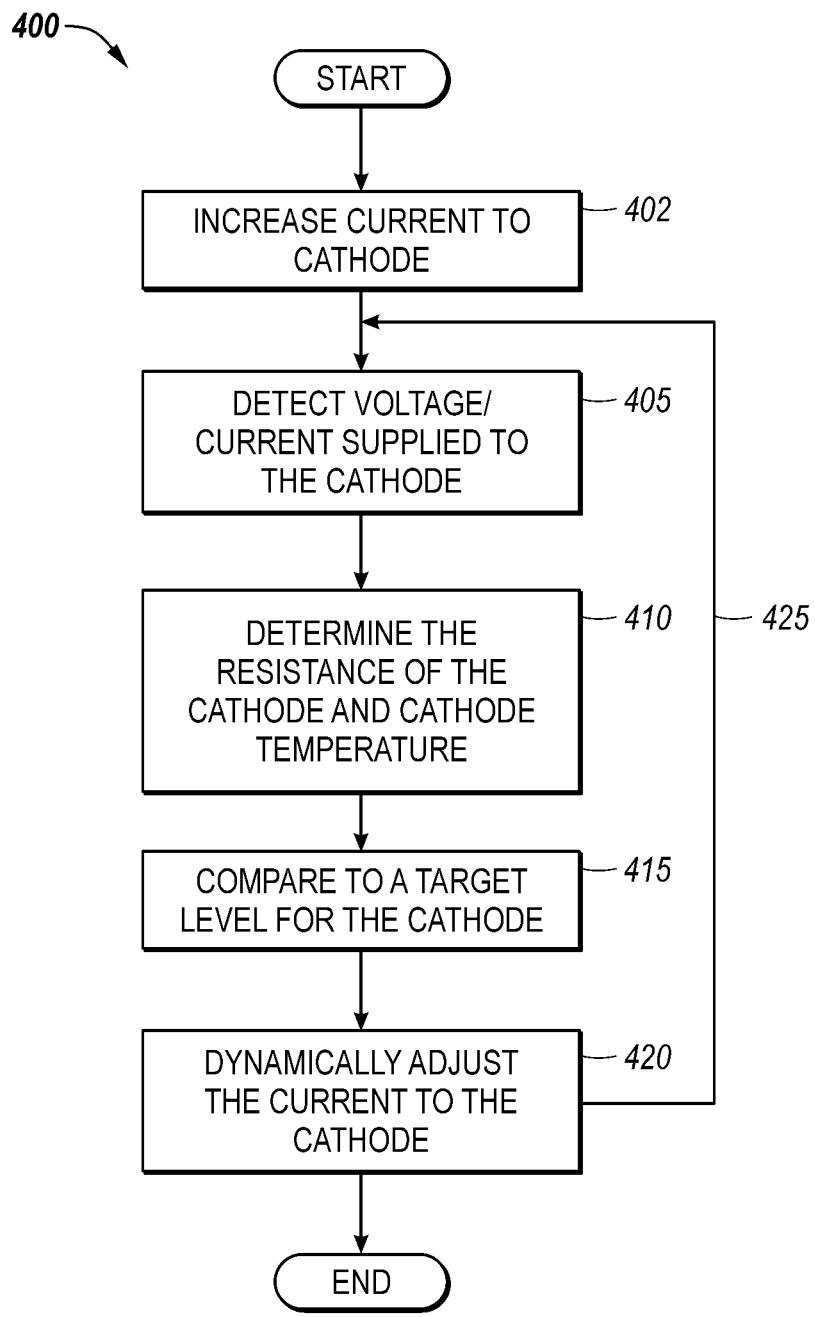
FIG. 4 shows a method of dynamically adjusting current provided to a cathode filament.

Turning to FIG. 4, there is shown a method according to the present disclosure when current is supplied to cathode 105 (step 402) from a cathode heating supply 113 to increase the amount of current responsive to a feedback signal. As a cathode ages or becomes contaminated, a desired emission current may require heating of the cathode to higher temperatures. However, if a cathode is heated too high it may fail. Thus, to avoid failure, the controller may reduce the emission current to a level less than the desired profile would indicate, avoiding failure at a cost of reduced sensitivity.

In one exemplary embodiment, the heating current to the cathode is controlled to raise emission current (step 402) as, for example, shown in one of the profiles of FIG. 2. The voltage access and the current through the cathode are detected (step 405), and a signal is delivered to the controller 105*a*. The controller 105*a*, using the voltage and the current readings, then determines the resistance of the cathode 105 and the cathode 105 temperature (step 410). The temperature can be compared to target temperature values for the cathode 105 (step 415) stored in memory 107. In operation, if the cathode 105 is adjusted, and if the temperature difference between a current temperature value and a target temperature value exceeds a threshold, then the emission current will not be adjusted the desired amount, and instead be dynamically adjusted to a different level to prevent damaging the cathode 105 (step 420) and also to reduce sputtering. Again, the dynamic adjustment can be made according to a specific formula, can be linear, can be over a number of steps, or can be made in a non-linear manner. Preferably, this data can be stored on a non-volatile memory 107 shown in FIG. 1. Memory 107 can also store a number of dynamic emission current profiles for various applications in response to the comparison 415.

It should be appreciated that several different cathode 105 materials or cathode 105 types and brands can be used with the ionization gauge 100. A cathode type or brand may be detected, and a signal delivered to the controller 105*a*. Sensor 240 can detect an amount of emitted light from the cathode 105, an infrared wave length, or an optical parameter of the light emitted from the incandescent cathode 105. The brand or material may be detected by a sensor, or the type may be input by a user.

The controller 105*a* using the signal, then determines the appropriate current supplied to the cathode 105 using reference levels to prevent stressing the cathode, or to reduce sputtering. In operation, if current supplied to the cathode 105 is adjusted, and if the cathode type or brand is detected, then the cathode 105 is dynamically adjusted to prevent damaging the cathode 105 based on an acceptable level to prevent stressing the particular cathode material and/or brand. Again, the dynamic adjustment can be made according to a specific formula, in a linear manner, over a number of steps, or in a non-linear manner.

Figure 5:
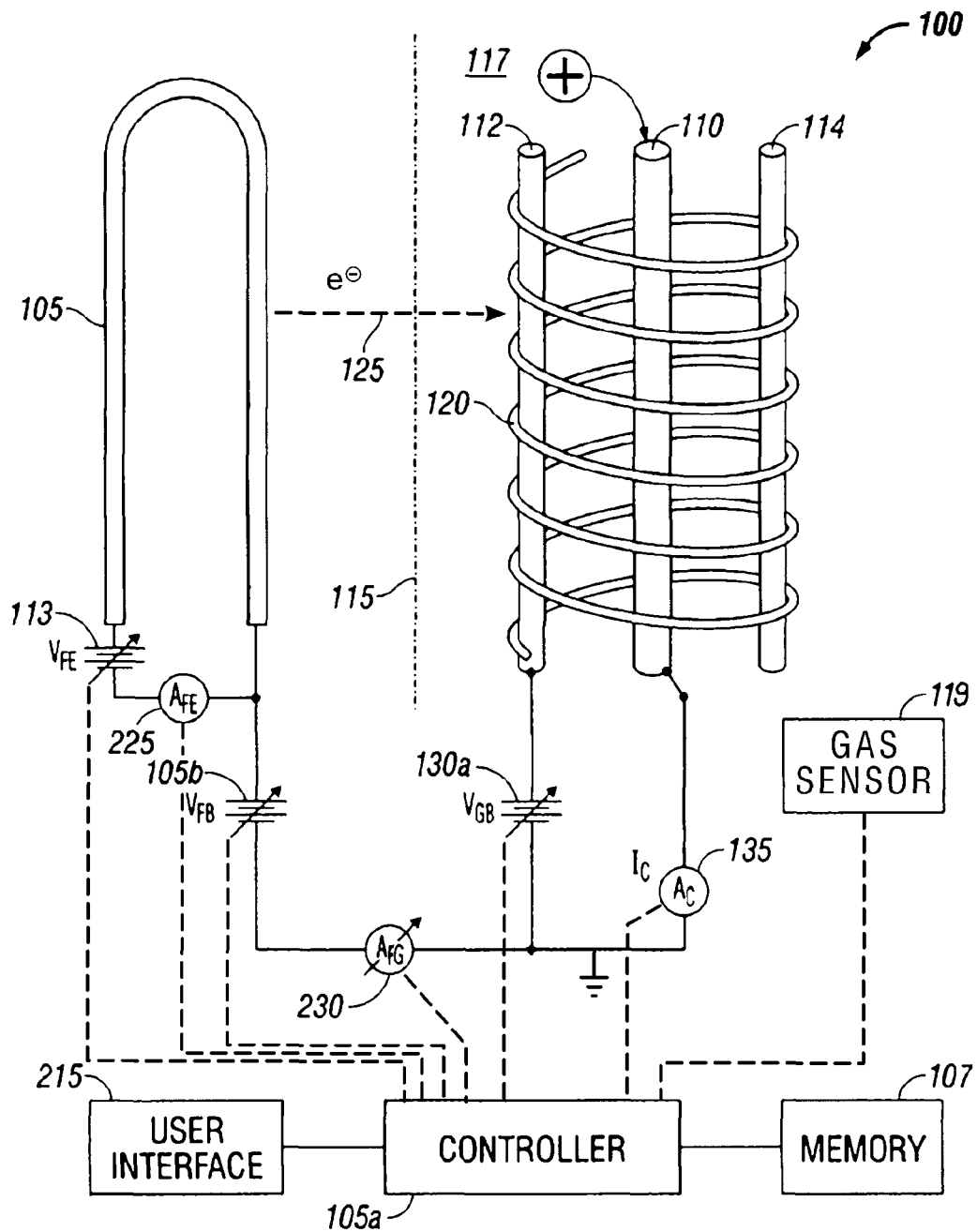
FIG. 5 shows an embodiment of an ionization gauge that includes a gas sensor.

Turning now to FIG. 5, in another exemplary embodiment according to the present disclosure, a gas species within the ionization gauge is detected, and a signal is delivered to the controller 105*a* indicative of the gas species. The gas species may be detected by a sensor 119 and a signal may be delivered to the controller 105*a* of the specific gas species or combination of species. The sensor 119, for example, may be an optical sensor or a residual gas analyzer. The controller 105*a*, using the signal, then determines the appropriate power supplied to the cathode 105 from the heating supply 113. The species of the gas can identify reference levels or a number of preset target emission current values stored in memory 107, which are obtained by the controller 105*a*, and then the controller 105*a* supplies appropriate heating current to the cathode 105. The target levels may be written to the non-volatile memory 107, which can be accessed by the controller 105*a*.

An operation time that the cathode 105 is operated may be monitored, and a signal is delivered to the controller 105*a* indicative of the time of operation of the cathode 105. The time may be recorded, or the time may be monitored continuously. In another embodiment, the time can be manually monitored and the time of operation can be manually input and delivered to the controller 105*s* in an acceptable digital format by a user. The controller 105*a*, using the time information, then determines the acceptable current levels supplied to the cathode 105. In operation, if current supplied to the cathode 105 is adjusted, and if the time of operation parameter exceeds a predetermined threshold indicating that the increase in current may stress or damage the cathode, then the cathode 105 is dynamically adjusted to prevent damaging the cathode 105. Again, the dynamic adjustment can be made according to a specific formula, in a linear manner, over a number of steps, or can be made in a non-linear manner as previously discussed.

In one embodiment, the collector current is maintained at a fixed minimum value for a pressure range. The emission current supplied by the cathode filament 105 is continuously adjusted by the controller 105a in a closed loop feed back control system to maintain the fixed level of collector current. A pressure change tends to change the collector current. That change is sensed by the controller, which adjusts the cathode emission current to counter the change in collector current, maintaining its fixed level.

In a further embodiment, the fixed collector electrode 110 current target values can be selectively chosen from a number of different current target values. Preferably, the target values are selected by a pressure range. This is to permit a high signal to noise ratio while minimizing the adjusted emission current for a previously specified pressure range.

Preferably, the ionization gauge 100 has a relatively small electron emission time constant, so that the emission current rate of change easily tracks and changes with the pressure.

In a further embodiment, the ionization gauge 100 may operate with a fixed collector current at some pressure ranges, and with a variable collector current at other different pressure ranges. At high pressures where the collector current provides adequate signal to noise ratio, a fixed collector current provides a strong signal for the controller 105a to continuously change the emission current depending on the pressure, so a change in pressure is now represented by a change in the emission current. At low pressures, the signal to noise ratio may be too low to form a strong signal in the collector electrode 110. Accordingly, at low pressures, the ionization gauge 100 may switch from using a fixed collector current to a variable collector current, and emission current is selected for optimum strength of the collector current. This allows for a more accurate measurement of the pressure at low pressures. At low pressures the gauge will then use the current from the collector electrode 110 to measure pressure.

In some instances, there may be an overlap between ranges of pressure where the measurement of pressure can occur successfully either with a fixed collector current and a variable emission current or with a variable collector current and a fixed emission current. Accordingly, the controller 105a may monitor one or more variables of the gauge 100 using an algorithm to correctly select the mode of operation at the overlap of pressure ranges based on the result of the algorithm. This is to prevent the continuous oscillation between a fixed collector current and a variable collector current mode in the pressure overlap region.

The ionization gauge 100 preferably can measure both base pressure (high vacuum) and higher processing pressures (mostly in the mTorr range); however, this is not limiting and various operational parameters for measurement are possible and within the scope of the present disclosure. The ionization gauge 100 can be used to measure pressure in the manufacture of flat panel displays, magnetic media operations, solar cells, optical coating operations, semiconductor manufacturing operations, and other manufacturing process operations. Such processes may include physical vapor deposition, plasma vapor deposition (PVD), chemical vapor deposition (CVD), atomic layer deposition (ALD), plasma etch operations, implantation operations, oxidation/diffusion, forming of nitrides, vacuum lithography, dry strip operations, epitaxy operations (EPI), rapid thermal processing (RTP) operations, extreme ultraviolet lithography operations, and others. Preferably, the ionization gauge 100 may also be operable with one or more analytical tools, such as, for example, a microscope or a mass spectrometer. Mass spectrometers may include gas chromatograph instruments (GC), liquid chromatograph instruments (LC), ion trap instruments, magnetic sector spectrometers instruments, double-focusing instruments, time-of-flight instruments (TOF), rotating field instruments, ion mobility instruments, linear quadrupole instruments, and others.

Surface analytical instruments that can be used in connection with the ionization gauge 100, and with or without a cluster tool may include scanning electron microscopes, energy dispersive X-ray spectroscopy instruments (EOS/XPS), scanning auger microanalysis instruments (Auger/SAM), glow discharge mass spectroscopy instruments (GDMS), electron spectroscopy for chemical analysis instruments (ESCA), atomic force microscopy/scanning probe microscopy instruments (AFM/SPM), Fourier transform infrared spectroscopy instruments (FTIR), wavelength dispersive X-ray spectroscopy instruments (WDS), inductively coupled plasma mass spectroscopy instruments (ICPMS), x-ray fluorescence instruments (XRF), neutron activation analysis instruments (NAA), metrology instruments, and others. It should be appreciated that this listing is not exhaustive and the gauge 100 may be used with other instruments not listed.

While this invention has been particularly shown and described with references to example embodiments thereof, it will be understood by those skilled in the art that various changes in form and details may be made therein without departing from the scope of the invention encompassed by the appended claims. For example, the invention may be applied to other forms of ionization gauges such as:

a Bayard-Alpert geometry with cathode outside and ion collector inside the anode;

a Triode gauge geometry with cathode inside and ion collector outside;

a Schultz-Phelps geometry with one flat plate as anode, one parallel flat plate as ion collector, and the cathode in between;

a high pressure gauge with an additional ion collector outside the anode for ions to be collected at high pressure when they are generated outside the anode.

Further, other electron sources such as cold cathode sources may be utilized. Also, the controller may be integral with a vacuum gauge or may be remote, for example, within programming of a host computer.

What is claimed is:

1. An ionization gauge to measure pressure in a process, the ionization gauge comprising:
    an electron source that emits electrons;
    an anode that defines an ionization space;
    a collector electrode to collect ions formed by an impact between the electrons and gas in the ionization space; and
    a controller that actively varies emission current from the electron source to a substantially different control level, during operation of the ionization gauge to measure pressure in a measurement chamber, in response to a user defined operating parameter of a specific process as the specific process is being performed by a tool, other than the ionization gauge, exposed to the measured pressure.

2. The ionzation gauge of claim 1, wherein the controller also controls emission current from the electron source as a function of pressure, in addition to controlling emission current in response to a user defined operating parameter.

3. The ionization gauge of claim 2, wherein the controller controls the emission current in a continuously variable manner based on pressure.

4. The ionization gauge of claim 2, wherein the function of pressure is selectable by a user.

5. The ionization gauge of claim 1, wherein the operating parameter is a species of gas in the environment being measured.

6. The ionization gauge of claim 1, wherein, in a first pressure range, collector current is held to a fixed level and, in a second pressure range, the collector current is allowed to vary.

7. The ionization gauge of claim 1, further comprising plural emission current profiles stored in memory and selected by a user.

8. The ionization gauge of claim 1, wherein a pressure signal is formed from the collected ions.

9. The ionization gauge of claim 1, wherein the operating parameter is a control signal that anticipates a change in pressure due to a process step.

10. A method of measuring a gas pressure in a process, the method comprising the steps of:
producing electrons from an electron source;
during operation of an ionization gauge to measure pressure, dynamically varying an emission current from the electron source to a substantially different control level based on a user defined operating parameter of a specific process as the specific process is being performed by a tool, other than the ionization gauge, exposed to the measured pressure;
transmitting the electrons through an anode defining an ionization space of the ionization gauge to form ions; and
collecting the ions in the ionization gauge.

11. The method of claim 10, further comprising controlling emission current from the electron source as a function of pressure, in addition to controlling emission current in response to a user defined operating parameter.

12. The method of claim 11, wherein the emission current is varied in a continuously variable manner based on pressure.

13. The method of claim 11, wherein the function of pressure is selected by a user.

14. The method of claim 10, wherein the operating parameter is a species of gas in the environment being measured.

15. The method of claim 10, wherein, in a first pressure range, collector current is held to a fixed level, and in a second pressure range, the collector current is allowed to vary.

16. The method of claim 10, wherein the emission current is varied based on one of plural emission current profiles stored in memory and selected by a user.

17. The method of claim 10, further comprising forming a pressure signal from the collected ions.

18. The method of claim 10, wherein the operating parameter is a control signal that anticipates a change in pressure due to a process step.

* * * * *